US009084757B2

(12) United States Patent
Ripamonti

(10) Patent No.: US 9,084,757 B2
(45) Date of Patent: Jul. 21, 2015

(54) OSTEOGENIC DEVICE FOR INDUCING BONE FORMATION IN CLINICAL CONTEXTS

(75) Inventor: Ugo Ripamonti, Parktown (ZA)

(73) Assignees: UNIVERSITY OF THE WITWATERSRAND, JOHANNESBURG, Johannesburg (ZA); RIPAMONTI, UGO BONE RESEARCH LABORATORY, FACULTY OF HEALTH SCIENCES, Parktown (ZA); MEDICAL RESEARCH COUNCIL OF SOUTH AFRICA, Cape Town (ZA)

( * ) Notice: Subject to any disclaimer, the term of this patent is extended or adjusted under 35 U.S.C. 154(b) by 312 days.

(21) Appl. No.: 13/463,018

(22) Filed: May 3, 2012

(65) Prior Publication Data

US 2012/0277879 A1    Nov. 1, 2012

Related U.S. Application Data

(62) Division of application No. 12/083,684, filed as application No. PCT/IB2006/002864 on Oct. 13, 2006, now abandoned.

(30) Foreign Application Priority Data

Oct. 17, 2005 (ZA) .................................. 2005/08378

(51) Int. Cl.

| A61K 38/18 | (2006.01) |
|---|---|
| A61K 35/32 | (2015.01) |
| A61K 35/34 | (2015.01) |
| C07K 14/495 | (2006.01) |
| A61L 27/36 | (2006.01) |
| A61L 27/22 | (2006.01) |
| A61L 27/54 | (2006.01) |

(52) U.S. Cl.
CPC ............. *A61K 38/1841* (2013.01); *A61K 35/32* (2013.01); *A61L 27/227* (2013.01); *A61L 27/3604* (2013.01); *A61L 27/3608* (2013.01); *A61L 27/54* (2013.01); *C07K 14/495* (2013.01); *A61L 2300/414* (2013.01); *A61L 2430/02* (2013.01)

(58) Field of Classification Search
None
See application file for complete search history.

(56) References Cited

U.S. PATENT DOCUMENTS

| 5,158,934 | A | 10/1992 | Ammann |
| 6,649,168 | B2 * | 11/2003 | Arvinte et al. ............. 424/198.1 |
| 2001/0038848 | A1 * | 11/2001 | Donda et al. .................. 424/423 |
| 2003/0143258 | A1 * | 7/2003 | Knaack et al. ................ 424/426 |
| 2003/0206937 | A1 | 11/2003 | Gertzman |

FOREIGN PATENT DOCUMENTS

| WO | WO 03/079964 | 10/2003 |
| ZA | 2002/2307 | 3/2002 |

OTHER PUBLICATIONS

Ghellal et al., Anticancer Res., 2000, vol. 20(6B):4413-4418.*
Mahari et al., Eur. Cells and Materials, 2003, vol. 5 (suppl. 1):47-48.*
Kao et al., Ophthalmic Surgery and Lasers, 1999, vol. 30(1):69-71.*
B. Mahari et al: "Dose-Effect of Transforming Growth Factor BETA3 on Degradation of Tricalcium Phosphate Ceramic", European Cells and Materials vol. 5. Suppl.1, pp. 47-48, May 14, 2003.
S. Kamakura et al., "Implantation of octacalcium phosphate combined with transforming growth factor-$\beta_1$ enhances bone repair as well as resorption of the implant in rat skull defects," Journal of Biomedical Materials Research, Jan. 1, 2001, vol. 57, No. 2, pp. 175-182.
Ripamonti et al. "Bone Morphogenetic Proteins in Craniofacial and periodontal tissue engineering: Experimental Studies in the Non-Human Papio ursinus." Cytokine & Growth Factor Reviews 16 (2005) pp. 357-368.
Ripamonti et al. "Bone Induction by BMPs/Ops and Related Family Members in Primates. The Critical Role of Delivery Systems." The Journal of Bone & Joint Surgery vol. 83-A, Supplement 1, Part 2, 2001, Pages Si 117-127.
Roberts et al. "Transforming Growth Factor type $\beta$: Rapid Induction of Fibrosis and Angiogenesis in vivo and Stimulation of Collagen Formation in virto." Proc. Natl. Acad. Sci. USA vol. 83, Jun. 1986, pp. 4167-4171.
Sampath et al. "Isolation of Osteogenin, an Extracellular Matrix-Associated, Bone-Inductive Protein, by Heparin Affinity Chromatography." Proc. Natl. Acad. Sci. USA vol. 84, Oct. 1987, pp. 7109-7113.
Hammonds et al. "Bone-Inducing Activity of Mature BMP-2b Produced from a Hybrid BMP-2a/2b Precursor." Molecular Endocrinology (1990) vol. 4:149-155.
Duneas et al. "Transforming Growth Factor-$\beta_1$: Induction of Bone Morphogenetic Protein Genes Expression During Endochondral Bone Formation in the Baboon, and Synergistic Interaction with Osteogenic Proteins-1 (BMP-7)." Growth Factors vol. 15, pp. 259-277. (1998).
Ripamonti et al. "Induction of Endochondral Bone Formation by Recombinant Human Transferring Growth Factor-$\beta 2$ in the Baboon (Papio ursinus)." Growth Factors (2000) vol. 17:269-285.
Ripamonti et al. "Limited Chondro-osteogenesis by Recombinant Human Transforming Growth Factor-$\beta_1$ in Calvarial Defects of Adult Baboons (Papio ursinus)." Journal of Bone and Mineral Research, vol. 11, No. 7, 1996, pp. 938-945.

(Continued)

*Primary Examiner* — Xiaozhen Xie
(74) *Attorney, Agent, or Firm* — Jacobson Holman, PLLC

(57) ABSTRACT

This invention relates to an osteogenic device for the de novo induction of bone formation in a mammal. The device contains at least one transforming growth factor-$\beta 3$ isoform and a retention matrix. The device is introduced by direct injection or surgical implantation into an area where de novo bone formation is desired and, once implanted, the retention matrix acts to retain the TGF-$\beta 3$ isoform at its place of introduction and forms a scaffold for generated bone, the induction of which is promoted by the TGF-$\beta 3$ isoform. The device may be used to induce bone growth where bone has been debrided in a surgical procedure and it may also be used to transform neoplastic primary and/or metastatic secondary masses into bone thus facilitating surgical debridement thereof.

12 Claims, 7 Drawing Sheets

(56) References Cited

OTHER PUBLICATIONS

Sampath et al. "Recombinant Human Osteogenic Protein -1 (hOP-1) Induces New Bone Formation in Vivo with a Specific Activity Comparable with Natural Bovine Osteogenic Proteing and Stimulates Osteoblast Proliferation and Differentiation in Vitro." The Journal of Biological Chemistry, vol. 267, Oct. 5, 1992, pp. 20352-20362.

Ripamonti et al. "Sintered Porous Hydrozyapatites with Intrinsic Osteoinductive Activity: Geometric Induction of Bone Formation." South African Journal of Science 95, Aug. 1999, pp. 335-343.

Sampath et al. "Dissociative Extraction and Reconstitution of Extracellular Matrix Components involved in Local Bone Differentiation." Proc. Natl. Acad. Sci, USA vol. 78, No. 12, Dec. 1981, pp. 7599-7603.

Ripamonti "Soluble Osteogenic Molecular Signals and the Induction of Bone Formation." Biomaterials vol. 27, (2006) pp. 807-822.

Ripamonti. "Osteogenice Proteins of the TGF-$\beta$ Superfamily." In Encyclopedia of Hormones. Eds. HL Henry, A W Norman, Academic Press, 2003, pp. 80-86.

Ripamonti et al. "Recombinant Transforming Growth Factor-$\beta$1 Induces Endochondral Bone in the Baboon and Synergizes with Recombinant Osteogenic Protein-1 (Bone Morphogenetic Protein-7) to Initiate Rapid Bone Formation." Journal of Bone and Mineral Research, vol. 12, No. 10, 1997, pp. 1584-1595.

Schnitzler et al. "Histomorphometry of Iliac Crest Trabecular Bone in Adult Male Baboons in Captivity." Calcif Tissue Int'l (1993) vol. 52, pp. 447-454.

* cited by examiner

OSTEOGENIC DEVICE FOR INDUCING BONE FORMATION IN CLINICAL CONTEXTS

This is a divisional application of U.S. patent application Ser. No. 12/083,684, filed Sep. 2, 2009, now abandoned, which is a U.S. national stage application of PCT/IB2006/002864, filed Oct. 13, 2006 and published in English, claiming the priority benefit of South Africa Patent Application No. 2005/08378, filed Oct. 17, 2005.

FIELD OF THE INVENTION

This invention relates to an osteogenic device for inducing de novo bone formation or osteogenesis in mammals, particularly primates, in clinical contexts.

BACKGROUND OF THE INVENTION

Skeletal bone defects of either the axial and craniofacial skeleton present formidable challenges to skeletal reconstructionists and to modern medicine. The mandible is a particularly difficult bone to repair and regenerate after surgical debridement of either neoplastic or inflammatory/infective lesions.

The surgical debridement of neoplastic masses of either primary or secondary metastatic tumours requires complex surgical procedures which are often unsuccessful in completely debriding the tumoral masses due to adhesion, metastatic growth and invasion into surrounding tissues, in particular vascular tissue. Unsuccessful debridement of neoplastic tumours leads to further secondary masses growth, invasion and metastatic tumoral growth with ultimate death.

Bone regeneration in clinical contexts requires three key components: an osteoinductive signal, a suitable substratum with which the signal is to be delivered and which acts as a scaffold for new bone to form, and host responding cells capable of differentiation into bone cells as a response to the osteoinductive signal. The signals responsible for osteoinduction are proteins collectively called the bone morphogenetic and osteogenic proteins (BMPs/OPs). BMPs/OPs are forming growth factor-β supergene family (TGF-β). The superfamily also includes four TGF-β isoforms, the transforming growth factor-β family per se [ref. 1-3 for reviews]. Members of both BMP/OP and TGF-β families are pleiotropic factors that, have potent and diverse effects on cell proliferation, differentiation, motility and matrix synthesis [1-3].

The three mammalian TGF-β isoforms (TGF-β1, β2 and β3) share limited homology with members of the BMP/OP family (BMP-2 through BMP-6 and osteogenic protein-1 and -2 [OP-1 and OP-2]) [1-3]. A striking and discriminatory feature of the BMPs/OPs is their ability to induce de novo cartilage and bone formation in extraskeletal heterotopic sites of a variety of animal models. Recombinant human (h) BMP-2, BMP-4 and OP-1 (also known as BMP-7) singly initiate endochondral bone formation in the subcutaneous space of the rat [1-3].

On the other hand, the TGF-β isoforms, either purified from natural sources or expressed by recombinant techniques, do not initiate endochondral bone formation in the in vivo bioassay in rodents [3-6].

Since TGF-β isoforms are most abundant in the extracellular matrix of bone as well as in many other tissues [3,4] and that the isoforms synergise in inducing large ossicles in the primate [1,3,7,8], the applicant envisages that the use of TGF-β isoforms in conjunction with a physiologically acceptable delivery vehicle is of paramount importance for inducing new bone formation in primates including man. Indeed, although BMPs/OPs can initiate bone formation following a single local application, the generation of new bone may not be rapid, and furthermore, substantial amounts of recombinantly produced BMPs/OPs may be required to achieve the desired effect in terms of bone volume and bone mass at site of skeletal defects.

Studies performed in rodents have shown that the TGF-β isoforms do not initiate bone formation when implanted in heterotopic extraskeletal sites [3-6]. In marked contrast, the applicant has shown that TGF-β1 and TGF-β2 induce endochondral bone formation when implanted heterotopically in the rectus abdominis muscle of adult primates of the genus *Papio* [3,7,8,9]. In calvarial defects, a site-specificity of induction of TGF-β1 and TGF-β2 has been found, however [3,9,10], i.e. with limited bone induction in calvarial defects and florid endochondral bone formation heterotopically in the rectus abdominis muscle of the primate *Papio ursinus*. In the same animal and implanting identical doses of TGF-β1 or TGF-β2, bone induction is florid in the rectus abdominis muscle but limited in calvarial defects [3,9,10,11].

This observed site and tissue-specificity of TGF-β isoforms in different tissue sites, i.e. the calvarium and the rectus abdominis muscle, may be explained by the paucity of TGF-β responding cells at the site of orthotopic calvarial implantation and/or by an increase expression of Smad-6 and Smad-7 gene products in calvarial sites down regulating the activity of the implanted TGF-β proteins [9, 11].

REFERENCES CITED

1. Ripamonti U. 2006 Soluble osteogenic molecular signals and the induction of bone formation. *Biomaterials* 27: 807-822.:737-744.
2. Ripamonti, U., Herbst, N.-N., Ramoshebi, L. N. 2005 Bone morphogenetic proteins in craniofacial and periodontal tissue engineering: Experimental studies in the non-human primate *Papio ursinus*. *Cytokine & Growth Factor Rev.* 16: 357-368.
3. Ripamonti, U., Ramoshebi, L. N., Matsaba, T., Tasker, J., Crooks, J., and Teare, 1. 2001. Bone induction by BMPs/OPs and related family members in primates. The critical role of delivery systems. *J. Bone Joint Surg. Am.* 83-A: Si 117-127.
4. Roberts, A. B., M. B. Sporn, R. K. Assoian, J. M. Smith, N. S. Roche, L. M. Wakefield, U. I. Heine, L. A. Liotta, V. Falanga, J. H. Kehrl, and A. S. Fauci. 1986. Transforming growth factor type B: Rapid induction of fibrosis and angiogenesis in vivo and stimulation of collagen formation in vitro. *Proc. Nail. Acad. Sd. USA*. 83:4167-4171.
5. Sampath, T. K., N. Muthukumaran, A. H. Reddi. 1987. Isolation of osteogenin, an extracellular matrix-associated bone-inductive protein, by heparin affinity chromatography. *Proc. Nail. Acad. Sci. USA.* 84:7109-7113.
6. Hammmonds, R. G., R. Schwall, A. Dudley, L. Berkemeier, C. Lai, J. Lee, N. Cunningham, A. H. Reddi, W. I. Wood, and A. J. Mason. 1991. Bone inducing activity of mature BMP-2b produced from a hybrid BMP-2a/2b precursor. *Mol. Endocrinol.* 5:149-155.
7. Ripamonti, U., Duneas, N., van den Heever, B., Bosch, C. and Crooks, J. 1997. Recombinant transforming growth factor-β1 induces endochondral bone in the baboon and synergizes with recombinant osteogenic protein-1 (bone morphogenetic protein-7) to initiate rapid bone formation. *J. Bone Miner. Res.* 12: 1584-1595.
8. Duneas, N., Crooks, J. and Ripamonti, U. 1998. Transforming growth factor-p 1: Induction of bone morphogenetic protein gene expression during endochondral bone formation in the baboon, and synergistic interaction with osteogenic protein-i (BMP-7). *Growth Factors* 15: 259-277.
9. Ripamonti, U., Crooks, J., Matsaba, T. and Tasker, 1. 2000. Induction of endochondral bone formation by recombinant human transforming growth factor-[32 in the baboon (*Papio ursinus*). *Growth Factors* 17: 269-285.
10. Ripamoni, U., Bosch, C., van den Heever, B., Duneas, N., Melsen, B. and Ebner, R. 1996. Limited chondro-osteogenesis by recombinant human transforming growth factor-β1 in calvarial defects of adult baboons (*Papio ursinus*). *J. Bone Miner. Res.* 11: 938-945.
11. Ripamonti U. 2003. Osteogenic proteins of the transforming growth factor-β superfamily. In Encyclopedia of Hormones (Eds. H L Henry, A W Norman, Academic Press pp 80-86, 2003 .
12. Sampath, T. K., J. C. Maliakal, P. V. Hauschka, W. K. Jones, H. Sasak, R. F. Tucker, K. H. White, J. E. Coughlin, M. M. Tucker, R. H. L. Pang, C. Corbett, E. Ozkaynak, H. Oppermann, and D. C. Rueger. 1992. Recombinant human osteogenic protein-i (hOP-i) induces new bone formation in vivo with a specific activity comparable with natural bovine osteogenic protein and stimulates osteoblast proliferation and differentiation in vitro. *J. Biol. Chem.* 267: 20352-20362.
13. Ripamonti, U., Crooks, J. and Kirkbride A. N. 1999. Sintered porous hydroxyapatite with intrinsic osteoinductive activity: geometric induction of bone formation. *S. Afr. J. Sci.* 95: 335-343.
14 Sampath, T. K., and A. H. Reddi. 1981. Dissociative extraction and reconstitution of extracellular matrix components involved in local bone differentiation. *Proc. Nati. Acad. Sci. USA.* 78:7599-7603.
15. Schnitzler, C. M., U. Ripamonti, J. M. Mesquita. 1993. Histomrphometry of iliac crest trabecular bone in adult male baboons in captivity. *Calcif Tiss. Int.* 52:447-454.

OBJECT OF THE INVENTION

It is an object of this invention to provide an osteogenic device for inducing de novo bone formation in mammals, particularly primates, in clinical contexts.

SUMMARY OF THE INVENTION

In accordance with this invention there is provided an osteogenic device for the de novo induction of bone formation in a mammal said osteogenic device comprising an effective concentration of at least one transforming growth factor (TGF) and a retention matrix, the device being introducible, in use, into a mammal at a site where de novo induction of bone is desired, the retention matrix acting to retain the TGF substantially at its place of introduction and to form a scaffold for generated bone, the induction of which is promoted by the TGF.

There is further provided for the osteogenic device to be delivered into the mammal by implantation, preferably by direct injection, alternatively by surgical implantation, into an area where de novo bone formation is desired.

There is also provided for the osteogenic device to be used to generate bone orthotopically, preferably at a site where bone has been removed such as, for example, in a debridement procedure carried out to treat neoplastic or inflammatory or infective lesions, particularly of the mandible in human primates. Alternatively there is provided for the osteogenic device to be used to generate bone heterotopically, preferably in the rectus abdominis muscle of a primate. Further alternatively there is provided for the osteogenic device to be used, when injected directly into neoplastic primary and/or metastatic secondary masses, to cause direct transformation of the neoplastic mass into bone thus facilitating surgical debridement thereof.

There is further provided for the osteogenic device to include morsellised muscle fragments, preferably rectus abdominis muscle fragments, which contain large numbers of responding cells. Alternatively there is provided for the osteogenic device to include morsellized fragments of bone, preferably autogenous bone. Further alternatively there is provided for the osteogenic device to include morsellised muscle and bone fragments.

There is also provided for the TGF to be a TGF-β isoform, preferably a TGF-β3 isoform, and further preferably, a human TGFβ3 isoform which may be a recombinant isoform.

A further aspect of the present invention provides a method of producing an osteogenic delivery vehicle for the de novo induction of bone formation in a mammal, said method comprising combining an effective concentration of a TGF and a retention matrix to form a delivery vehicle which is introducible, in use, into a mammal at a site where de novo induction of bone is desired, the retention matrix acting to retain the TGF substantially at its place of introduction and to form a scaffold for generated bone, the induction of which is initiated by the TGF.

There is further provided for the osteogenic delivery vehicle to be deliverable into the mammal by implantation, preferably by direct injection, alternatively by surgical implantation, into an area where de novo bone formation is desired.

There is also provided for the osteogenic delivery vehicle to be used to generate bone orthotopically, preferably at a site where bone has been removed such as, for example, in a debridement procedure carried out to treat neoplastic or inflammatory or infective lesions, particularly of the mandible in human primates. Alternatively there is provided for the osteogenic device to be used to generate bone heterotopically, preferably in the rectus abdominis muscle of a primate. Further alternatively there is provided for the osteogenic device to be used, when injected directly into neoplastic primary and/or metastatic secondary masses, to cause direct transformation of the neoplastic mass into bone thus facilitating surgical debridement thereof.

There is further provided for the osteogenic delivery vehicle to include morsellised muscle fragments, preferably rectus abdominis muscle fragments, which contain large numbers of responding cells. Alternatively there is provided for the osteogenic delivery vehicle to include morsellized fragments of bone, preferably induced autogenous bone. Further alternatively there is provided for the osteogenic delivery vehicle to include morsellised muscle and bone fragments.

There is also provided for the TGF to be a TGF-β isoform, preferably a TGF-β3 isoform, and further preferably, a human TGF-β3 isoform which may be a recombinant isoform.

Another aspect of the present invention provides for the use of an effective concentration of a TGF and a retention matrix in the manufacture of osteogenic device for use in the de novo induction of bone formation in a mammal comprising introducing said osteogenic device into the mammal at a site where de novo induction of bone is desired, the retention matrix acting to retain the TGF substantially at its place of introduction and to form a scaffold for generated bone, the induction of which is promoted by the TGF.

There is further provided for the osteogenic device to be deliverable into the mammal by implantation, preferably by direct injection, alternatively by surgical implantation, into an area where de novo bone formation is desired.

There is also provided for the osteogenic device to be usable to generate bone orthotopically, preferably at a site where bone has been removed such as, for example, in a debridement procedure carried out to treat neoplastic or inflammatory or infective lesions, particularly of the mandible in human primates. Alternatively there is provided for the osteogenic device to be used to generate bone heterotopically, preferably in the rectus abdominis muscle of a primate. Further alternatively there is provided for the osteogenic device to be used, when injected directly into neoplastic primary and/or metastatic secondary masses, to cause direct transformation of the neoplastic mass into bone thus facilitating surgical debridement thereof.

There is further provided for the osteogenic device to include morsellised muscle fragments, preferably rectus abdominis muscle fragments, which contain large numbers of responding cells. Alternatively there is provided for the osteogenic device to include morsellized fragments of bone, preferably induced autogenous bone. Further alternatively there is provided for the osteogenic device to include morsellised muscle and bone fragments.

There is also provided for the TGF to be a TGF-$\beta$ isoform, preferably a TGF-$\beta$3 isoform, and further preferably, a human TGF-$\beta$3 isoform which may be a recombinant isoform.

A further aspect of the present invention provides for a method of inducing de novo bone formation in a mammal comprising introducing an above described osteogenic device into a mammal at a site where de novo induction of bone is desired, either at a site where bone has been removed, alternatively at a heterotopical site, preferably within the rectus abdominis muscle which heterotopically produced bone is usable in forming bone grafts and the like.

The present invention also provides for a method of treating cancer comprising injecting an above described osteogenic device directly into neoplastic primary and/or metastatic secondary masses, inducing the transformation of the mass into bone and surgically debriding the transformed mass.

BRIEF DESCRIPTION OF THE INVENTION AND ITS PREFERRED EMBODIMENTS

The present invention and its preferred embodiments are now described with reference to the accompanying non limiting examples and figures in which.

Figure 6:
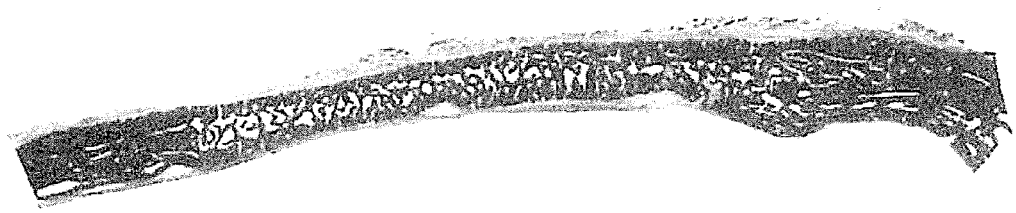
Figure 7:
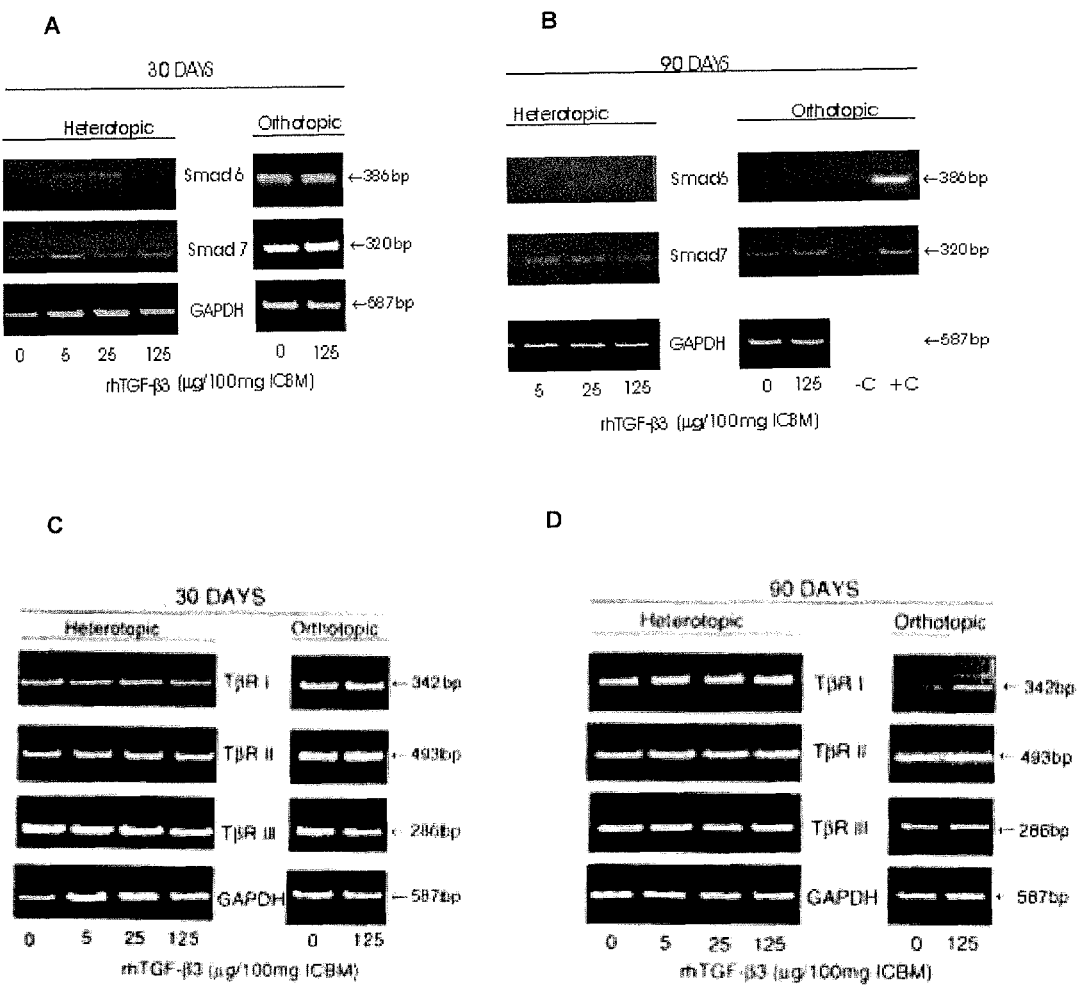
Figure 8:
Figure 9:
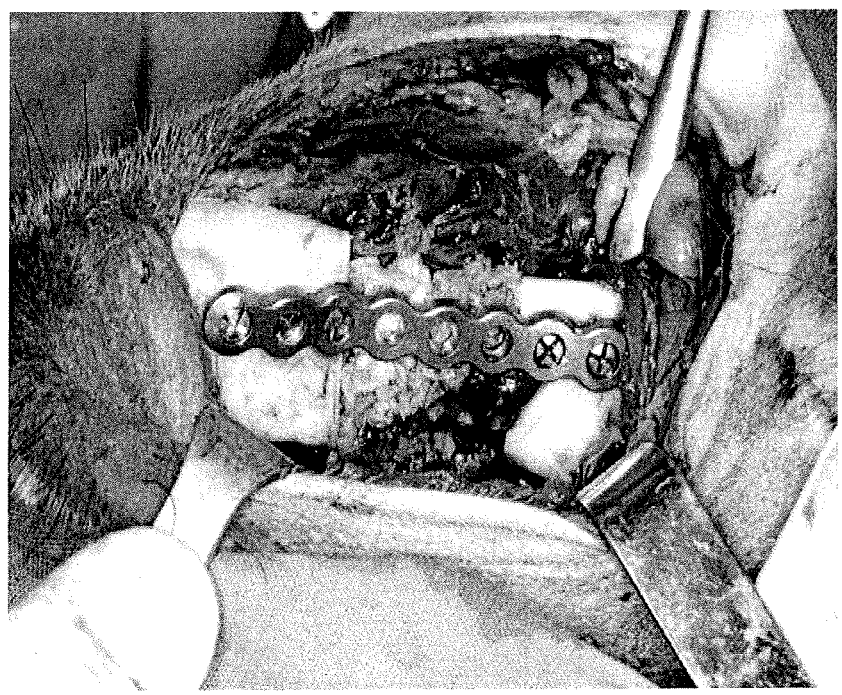

FIG. 6 is a photomicrograph of a histological section of a calvarial specimen upon implantation of 125 µg hTGF-$\beta$3 delivered by insoluble collagenous bone matrix as a physiologically acceptable delivery vehicle with the addition of morsellised fragments of rectus abdominis and harvested 90 days after implantation in an adult primate. Osteogenesis is found across the specimen and both pericranially and endocranially;

FIG. 7 is a composite photograph depicting the messenger RNA expression of Smad-6 and Smad-7 as determined by polymerase chain reaction (PCR) showing that the inhibitory gene products Smad-6 and Smad-7 are poorly expressed in ossicles generated heterotopically in the rectus abdominis by the osteogenic device and highly expressed on the other hand in tissue harvested from orthotopic calvarial defects. Panels A and B show mRNA expression of the inhibitory gene products Smad-6 and Smad-7 on day 30 and 90, respectively. The dramatic difference between heterotopic rectus abdominis and calvarial orthotopic mRNA expression clearly indicates the mechanistic insights of the site and tissue specificity of bone induction of the osteogenic device of the present invention in the rectus abdominis muscle vs calvarial sites. Panels C and D depict mRNA expression of the ligand receptors as evaluated by PCR in both heterotopic and orthotopic specimens of the primate *Papio ursinus*;

FIG. 8 is a clinical macrophotograph depicting fragments of morcellized bone after the harvesting of induced heterotopic ossicles generated in the rectus abdominis muscle of adult primates *Papio ursinus* upon the implantation of 125 µg doses of the hTGF-$\beta$3 isoform in the rectus adoininis muscle;

FIG. 9 is a clinical photograph depicting the full thickness segmental mandibular defect of a primate *Papio ursinus* transplanted with morcellized fragments of autogenous bone previously induced in the rectus abdominis muscle by 125 µg hTGF-$\beta$3 osteogenic device.

Figure 10:
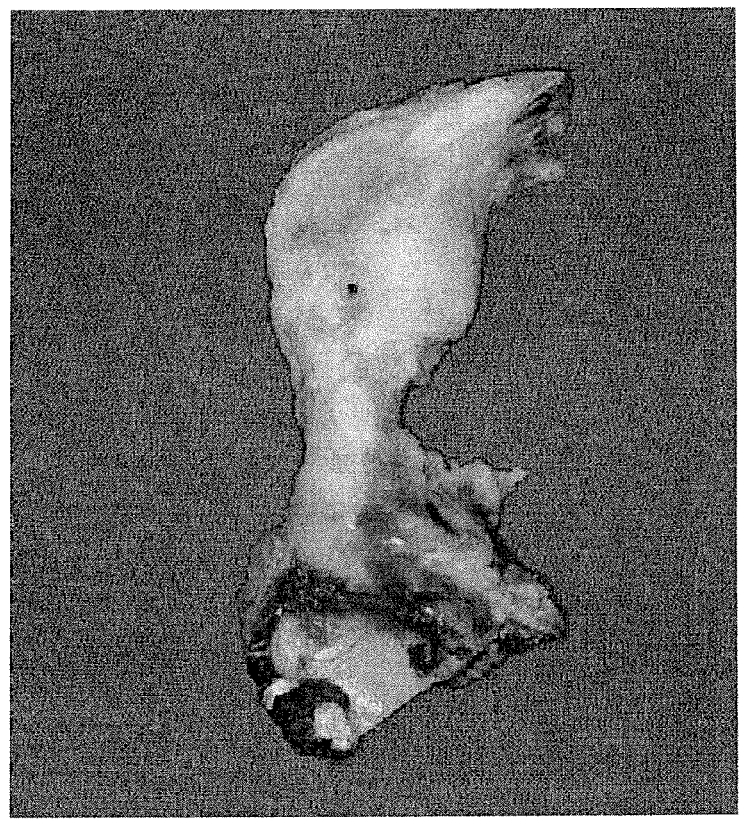
Figure 11:
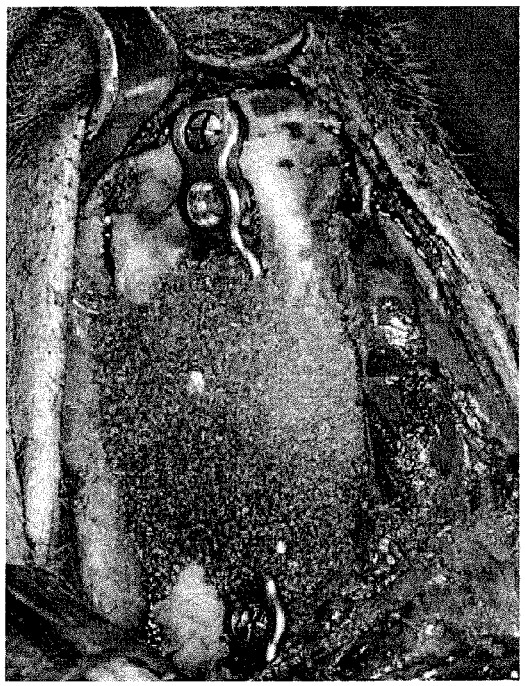
Figure 12:
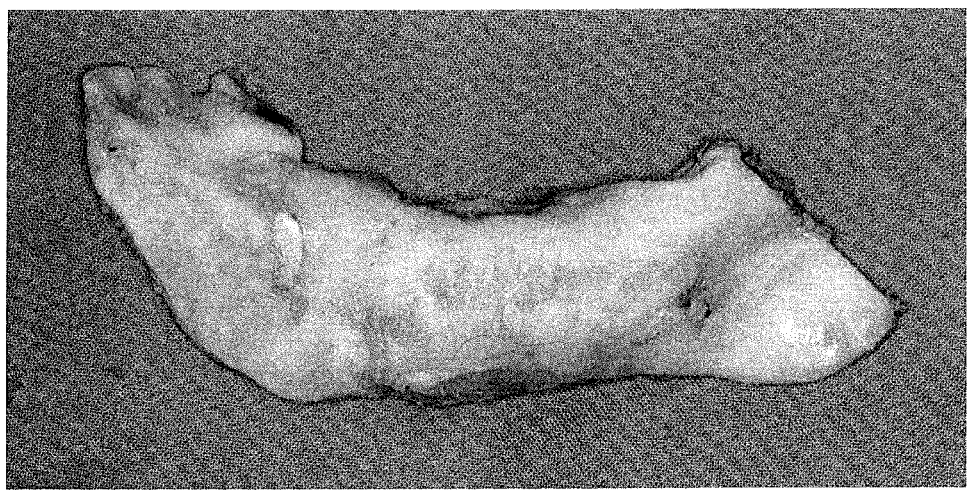

FIG. 10 is the clinical photograph of the treated mandibular defect 30 days after implantation of the newly formed and fragmented ossicle induced by doses of the hTGF-$\beta$3 osteogenic device showing regeneration and corticalization of the newly formed mandibular bone;

FIG. 11 is the clinical photograph depicting a mandibular full thickness segmental defect treated with 125 µg doses of the hTGF-$\beta$3 osteogenic device delivered by grams of insoluble collagenous bone matrix; and FIG. 12 is the clinical macrophotograph of the treated defect 30 days after implantation of the 125 µg hTGF-$\beta$3 osteogenic device showing complete regeneration of the segmental defect.

DETAILED DESCRIPTION OF INVENTION AND ITS PREFERRED EMBODIMENTS

In the following non-limiting examples, the following morphogens and biomimetic matrices as physiologically acceptable delivery vehicles were used: recombinant human transforming growth factor-$\beta$3 (hTGF-$\beta$3), physiologically acceptable delivery vehicles, i.e. insoluble collagenous matrix, demineralized bone matrix, biphasic sintered tricalcium phosphate and hydroxyapatite in a ratio of 40 to 60 and 60 to 40, respectively and highly crystalline sintered porous hydroxyapatite biomimetic matrix [13], 5 mM hydrochloric acid and morsellised fragments of rectus abdominis muscle. hTGF-β3 is prepared by recombinant techniques. Stock solutions hTGF-β3 were prepared in 5 mM hydrochloric acid. For a therapeutic perspective, a carrier matrix is required for the local delivery of hTGF-β3 to evoke a desired osteogenic response. As one of physiologically acceptable delivery vehicles, a collagenous bone matrix was used for the preparation of the osteogenic device. Collagenous bone matrix was prepared from diaphyseal segments of baboon and bovine cortical bones. After demineralization, the bone matrix was dissociatively extracted in 4 M guanidinium-HCl (Gdn-HCl), containing protease inhibitors [14]. The resulting insoluble collagenous matrix, inactive after extraction of osteogenic proteins, was washed twice with distilled water, dehydrated in ethanol and ether, and used as carrier for TGF-β3.

For the preparation of samples suitable for extraskeletal heterotopic implantation in the primate *Papio ursinus*, hTGF-β3 dissolved in 5 mMi hydrochloric acid was combined with insoluble collagenous bone matrix and lyophilized. To further improve the osteogenic activity of the hTGF-β3 osteogenic device, hTGF-β3 was also combined with allogeneic demineralized bone matrix so as to exploit the synergistic interaction with BMPs/OPs contained within the demineralized bone matrix [1,3,7,8,11]. Three doses of hTGF-β3 were used: 5, 25 and 125 μg of hTGF-β3 per 100 mg of carrier matrix. hTGF-β3 dissolved in 5 mM hydrochloric acid was also combined with discs of highly crystalline sintered porous hydroxyapatite for heterotopic extraskeletal implantation. For the preparation of the osteogenic device suitable for skeletal orthotopic implantation, hTGF-β3 in 5 mM hydrochloric acid was added to 1 gram of insoluble collagenous bone matrix for implantation in non-healing calvarial defects 25 mm in diameter of adult primates *Papio ursinus*, 25 and 125 μg hTGF-β3 per I gram of carrier matrix. Fragments of morsellised rectus abdominis muscle were added to the insoluble collagenous matrix containing doses of hTGF-β3 to form the osteogenic device. Doses of 125 μg hTGF-β3 combined with grams of insoluble collagenous bone matrix and/or demineralized bone matrix were implanted in segmental mandibular defects of the primate *Papio ursinus*.

Doses of hTGF-μ3 were also implanted bilaterally in ventral intramuscular pouches created by sharp and blunt dissection in the rectus abdominis muscle of the primate *Papio ursinus*. Implants were harvested on day 30 and 90 after surgery. The greater portion of each specimen was processed for undecalcified and decalcified histology and serial sections, cut at 4 μm, were stained using the free-floating method with Goldners trichrome for undecalcified bone. Consecutive sections were mounted and stained with 0.1% toluidine blue in 30% ethanol for histological visualization of cartilage. Histological sections were analyzed to determine the mineralized bone, osteoid, and residual collagenous matrix volumes (in %). The cross sectional area (in mm$^2$) of newly generated tissue (mineralized bone, osteoid, and bone marrow) in each specimen was also measured [8,9]. Remaining tissues were pooled, crushed and total RNA was isolated as described [8,9]. Materials and methods for preparation of Northern blot analyses and complementary DNA (cDNA) probes used were as described [8,9]. cDNA for Smad-6 and Smad-7 were used, as Smad-6 and -7 gene products are inhibitors of the vertebrate Smad-based TGF-β signalling pathways [3,9,11]. Receptors of the ligand were also used and evaluated on day 30 and 90 as shown in FIG. 7, Panels C and D.

Figure 1:
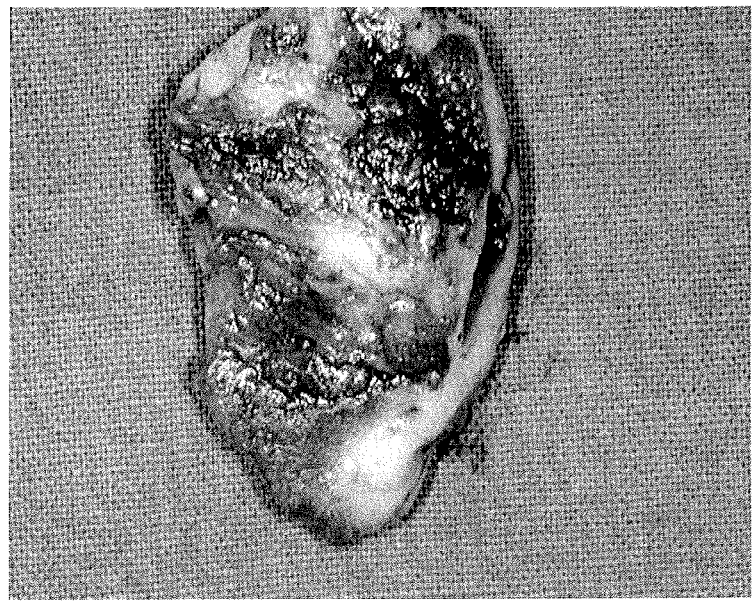
FIG. 1 is a clinical photomacrograph illustrating the induction of a large corticalized ossicle upon the implantation of 125 µg hTGF-$\beta$3 and delivered by insoluble collagenous bone matrix as a physiologically acceptable delivery vehicle and harvested from the rectus abdominis 30 days after implantation in an adult primate.
Figure 2:
FIG. 2 is a photomicrograph of a histological section of the ossicle shown in FIG. 1 with large quantities of newly formed and mineralized bone in blue with large osteoid seams in orange/red upon the implantation of 125 µg hTGF-$\beta$3 and delivered by insoluble collagenous bone matrix as carrier.

The osteogenic device made of combinations of hTGF-β3 delivered by both insoluble collagenous matrix or sintered porous hydroxyapatite and implanted extraskeletally in the rectus abdominis muscle resulted in the generation of massive ossicles displacing both the dorsal and ventral fasciae of the rectus abdominis. Cut surfaces showed mineralization of the external cortex and were red-brownish in the gross indicating bone marrow and associated highly vascular tissue. Mineralization of the newly formed enveloping cortex was evident as early as day 30 after implantation of 25 μg hTGF-β3. Implantation of 125 μg hTGF-β3 delivered by 100 mg of insoluble collagenous bone matrix resulted in the induction of massive corticalized mineralized ossicles of several cm in diameter within the rectus abdominis muscle. Histological analysis on undecalcified sections showed corticalization and mineralization of newly formed bone with extensive osteoid deposition on mineralized trabeculae as illustrated in FIG. 1. Implantation of 25 μg and 125 μg hTGF-β3 delivered by sintered porous hydroxyapatites and harvested on day 90 after implantation in the rectus abdominis muscle generated large ossicles with extensive bone formation surrounding the porous hydroxyapatite biomatrices as shown in Sheet FIG. 2 and FIG. 3. Interestingly, cartilage was observed within porous spaces of the hydroxyapatite biomatrices as aggregation of chondroblastic cells on specimens harvested on day 90 from the rectus abdominis muscle.

It is particularly important to point out that specimens of collagenous matrix or sintered porous hydroxyapatite which were treated with 25 and 125 μg of hTGF-β3 induced bone formation on day 30 and 90 in the adult primate *Papio ursinus*. In previous studies in rodents, when hTGF-β3 or other TGF-β isoforms were implanted in heterotopic sites, it induced mesenchymal cell recruitment and angiogenesis only but failed to initiate cartilage and bone formation [3-6]. These observations have indicated that hTGF-β3 alone do not initiate the cascade of bone induction. The generation of heterotopic bone formation in the primate by hTGF-β3 in the present patent application is noteworthy and underscores the critical role of animal models in bone induction [3].

Figure 3:
FIG. 3 is a photomicrograph of a histological section of large quantities of newly formed bone upon the implantation of 125 µg hTGF-$\beta$3 and delivered by highly crystalline sintered porous hydroxyapatite as a physiologically acceptable delivery vehicle and harvested from the rectus abdominis 90 days after implantation in an adult primate.
Figure 4:
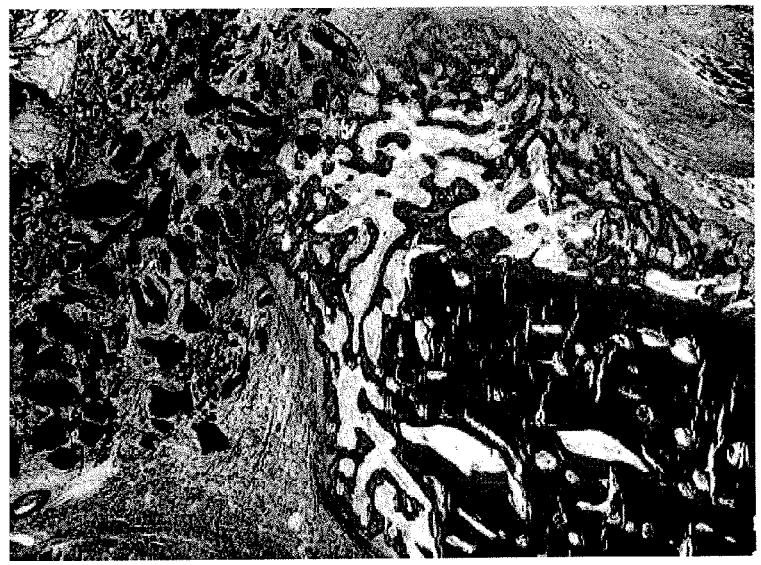
FIG. 4 is a photomicrograph of a histological section of a calvarial specimen upon implantation of 125 µg hTGF-$\beta$3 delivered by insoluble collagenous bone matrix as a physiologically acceptable delivery vehicle and harvested 30 days after implantation in an adult primate showing complete lack of bone formation at the interface of the defect.
Figure 5:
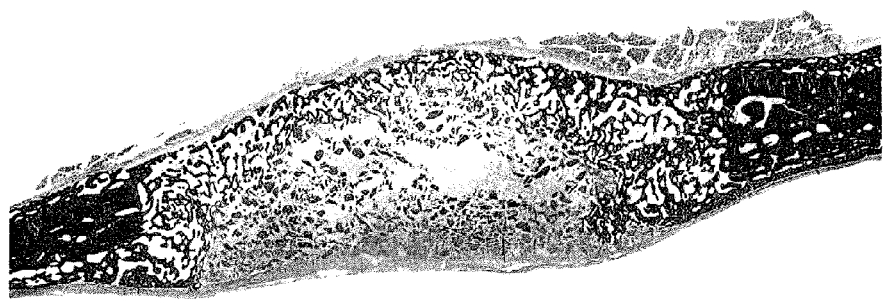
FIG. 5 is a photomicrograph of a histological section of a calvarial specimen upon implantation of 125 µg hTGF-µ3 delivered by insoluble collagenous bone matrix as a physiologically acceptable delivery vehicle and harvested 90 days after implantation in an adult primate. Limited osteogenesis is found across the specimen and with bone formation only pericranially.

Implantation of doses of hTGF-β3 delivered by the insoluble collagenous matrix in non-healing calvarial defects of the primate *Papio ursinus* showed lack of bone formation on undecalcified sections prepared on day 30 after implantation as shown in FIG. 3. On day 90 bone formation in hTGF-β3 calvarial specimens remained limited, with a scattered zone of osteogenesis below the pericranium FIG. 5. Histological analysis of specimens treated with 125 μg hTGF-β3 showed osteogenesis albeit to a limited extent across the treated defects but only pericranially FIG. 5.

Histological analysis revealed a recurrent pattern of histological features as seen extending from the pericranial to the endocranial surfaces of the specimens. The specimens facing the pericranium showed newly-formed and mineralized bone with osteoclastic activity facing the pericranium. Just below the mineralized bone there was more trabecular woven bone with large osteoid seams and a marked vascular component. The subjacent inactive collagenous bone matrix supported the newly formed bone and rested above an area of loose fibrovascular tissue, with scattered particles of collagenous carrier. The endocranial layer was characterized by the presence of more compact but inactive collagenous matrix ending just above the dura mater FIG. 5.

On the other hand, implantation of 125 μg hTGF-β3 in full thickness segmental mandibular defects showed bone induction and corticalization of the newly formed bone as shown in FIG. 12. Substantial bone regeneration was also observed in mandibular segmental defects implanted with morcellized bone fragments of newly induced ossicles by the hTGF-β3 osteogenic device in the rectus abdominis muscle.

The most striking results are that the bone inductive activity of the hTGF-β3 isoform in the primate is site and tissue specific, with rather substantial bone induction in heterotopic sites i.e. the rectus abdominis muscle but limited osteinductivity in non-healing calvarial defects. The addition of morsellised fragments of rectus abdominis muscle cells and the reconstitution of the hTGF-β3 isoform combined with physiologically acceptable delivery systems with morsellised muscle fragments restored the osteogenic activity of the TGF-β3 isoform in cranial sites and constitutes one aspect the osteogenic device of the present invention.

With the primate under general anaesthesia, pouches are created in the rectus abdominis muscle by sharp and blunt dissection. Before implantation of the hTGF-β3 osteogenic device, a fragment of rectus abdominis muscle tissue is harvested by sharp dissection: 2 cm in length and 0.5 cm in diameter. The fragment is placed on a hard sterilized surface and using two scalpels is morsellised to form a paste of fragmented muscle and cells. The above can also be achieved by freezing the fragment in liquid nitrogen and the frozen muscle is then fragmented to small cellular pieces with a sterile mortar and pestle. Fragments containing multiple rectus abdominis muscle cells are then added to the insoluble collagenous bone matrix containing doses of hTGF-β3 isoform and mixed with 1 gram of the insoluble matrix additionally blended by adding 300 μl of sterile dehyonized water to facilitate the implantation to the bone defect. Specimens treated with the osteogenic device as described were implanted in calvarial defects of the primate *Paplo ursinus* to demonstrate the therapeutic utility of the osteogenic device for bone repair and regeneration. Specimens were harvested 30 and 90 days after implantation. Undecalcified sections of the specimens showed bone induction across the defect FIG. 6 and areas of chondrogenesis in the membranous bone of the calvaria. The addition of muscle cells restored the biological activity of the hTGF-β3 isoform and induced a sequential cascade of events as seen in heterotopic specimens, i.e. the induction of endochondral bone and in bones of membranous origin as the calvaria.

In full-thickness mandibular segmental defects, the hTGF-β3 osteogenic device can directly induce bone formation even without the addition of rectus abdominis cells/fragments.

Expression patterns of Smad-6 and Smad-7 mRNAs reveal limited expression in heterotopic extraskeletal sites and over expression in orthotopic calvarial sites, i.e. calvarial defect specimens, indicating that over expression of Smad-6 and Smad-7 down regulate the osteoinductive activity of the hTGF-3 osteogenic device when implanted in calvarial defects FIG. 7 (Panels A and B). Ligand's receptors analyses on day 30 and 90 are shown in FIG. 7 Panels C and D indicating receptors' expression both heterotopically and orthotopically.

The described osteogenic device demonstrates the restoration of the osteogenic activity of the TGF-β3 isoform in calvarial sites by reconstituting the TGF-β3 isoform with morsellised fragments of rectus abdominis muscle which provides the responding cells for the sequential induction cascade by the hTGF-β3 isoform. The osteogenic device is capable of inducing rapid new bone formation in skeletal sites of the primate in a manner which supersedes bone formation capabilities of BMPs/OPs. Rapid bone formation is achieved by adding a multitude of responding cells with specific cell surface receptors for the TGF-β3 isoform, harvested from the rectus abdominis muscle of the same primate, whereby new bone formation is raised several fold as compared to the isoform alone.

Still further, the present patent application demonstrates bone induction by the hTGF-β3 isoform in heterotopic sites of the primate, a biological activity as yet unreported in any animal species so far tested using the TGF-β3 isoform. The rapid endochondral bone induction by the hTGF-β3 isoform can be used for the generation of large ossicles, as shown in FIG. 1 in the rectus abdominis muscle of human patients. Generated ossicles are then harvested 30 days after heterotopic implantation and morsellised fragments of the newly generated bone are transplanted into bony defects affecting the same patient, defects either of the axial and craniofacial skeleton including periodontal osseous defects.

The rapid and massive induction of endochondral bone formation by the described osteogenic device in heterotopic extraskeletal sites is used for the transformation into bone of neoplastic and metastatic tumoral masses of mammals including humans with surgical delineation of the surgical masses to be surgically enucleated as well as with reduction and complete inhibition of biochemical paraneoplastic parameters after tissue transformation into bone.

A major advantage of the invention, at least as exemplified, is the capacity of the inventive osteogenic device to induce rapid bone formation and to induce a greater amount of bone formation both in extraskeletal heterotopic and skeletal orthotopic sites. It is of great importance to note that the invention provides an osteogenic device for oncologic, orthopaedic, craniofacial and periodontal applications that is capable of rapid bone formation when implanted into the primate *Papio ursinus*, a primate that has bone physiology and remodelling comparable to man [15], the ultimate recipient of the osteogenic device of the present invention. The rapidity of tissue morphogenesis and induction of bone formation complete with mineralization of the outer cortex of the ossicles and bone marrow formation by day 30 is of particular importance for osseous transformation of neoplastic masses and repair and regeneration of bone in the elderly, where repair phenomena are temporally delayed and healing progresses slower than in younger patients.

It will be understood that the invention herein is disclosed for the purpose of illustration and does not constitute departures from the spirit and scope of the invention, in particular, the composition of the osteogenic device is not limited to hTGF-β3 but extend to the other TGF-β isoforms including the amphibian TGF-β5 isoform which has been shown to be osteoinductive in the rectus abdominis muscle of adult primates at doses of 5 μig per 100 mg of collagenous matrix as carrier and extends to all BMP/OP family members (BMP-2 through BMP-14) and the newly chracterized TGF-β superfamily member i.e. Ebaf/Lefty-A , singly or in combination. Furthermore, the application of the osteogenic device is not limited to the transformation of neoplastic tumours into bone for rapid surgical debridement and to local applications where bone growth and regeneration is desired (i.e. at a bone defect site), but extend to specific administration using local injection routes for restoration of systemic bone loss in conditions such as osteoporosis.

In particular, this invention extends to the osteogenic device composed of osteogenic proteins of the TGF-β superfamily i.e. hBMPs/OPs and TGF-βs and specifically hTGF-β3 to be injected locally for the treatment of systemic bone loss, i.e. hTGF-3 in conjunction with the delivery system of Matrigel and morsellised rectus abdominis cellular fragments as exemplified in South African patent number 2002/2307 and PCT WO 03/079964 patent applications both entitled *Composition for Stimulating* de novo *Bone Induction*.

This invention describes an osteogenic device made of a combination of the hTGF-β3 isoform, the most powerful inducer of endochondral bone formation so far tested and found in primate species. The endochondral osteoinductivity of the TGF-β3 isoform has been discovered yet never published after implementation of research experiments in 1999 as per the relevant record book. The osteogenic device as described supersedes the bone inductive capabilities of the previously known osteogenic BMPs/OPs and as such, the device as presented, is a paradigmatic shift from EMPs/OPs to the TGF-3 isoform for rapid craniofacial and axial skeletal regeneration.

The above studies were conducted according to the Guidelines for the Care and Use of Experimental Animals prepared by the University of the Witwatersrand, Johannesburg in compliance with the National Code for Animal Use in Research, Education and Diagnosis in South Africa. Research protocols were approved by the Animal Ethics Screening Committee of the University.

The invention claimed is:

1. A method of inducing bone formation in a mammal, the method comprising introducing an effective amount of a composition comprising Transforming Growth Factor-beta 3 (TGF-β3) and a retention matrix into a mammal at a site where formation of bone is desired, wherein the bone formation is induced at a heterotopic site and wherein the site is a neoplasitc primary and/or metastatic secondary mass and the composition induces transformation of the mass into bone.

2. The method of claim 1, wherein the retention matrix retains the TGF-β3 substantially at its place of introduction and forms a scaffold for generated bone, and the TGF-β3 promotes the induction of bone.

3. The method of claim 1, which further comprises the step of surgically debriding the transformed mass.

4. The method of claim 1, wherein the composition is introduced into the mammal by implantation.

5. The method of claim 4, wherein the composition is surgically implanted into the mammal.

6. The method of claim 1, wherein the composition further includes morsellised muscle fragments.

7. The method of claim 6, wherein the muscle fragments are rectus abdominis muscle fragments.

8. The method of claim 1, wherein the composition further includes morsellized bone fragments.

9. The method of claim 8, wherein the bone fragments are autogenous bone fragments.

10. The method of claim 1, wherein the TGF-β3 is human TGF-β3.

11. The method of claim 10, wherein the human TGF-β3 is a recombinant human TGF-β3.

12. A method of inducing bone formation in a mammal, the method comprising introducing an effective amount of a composition comprising Transforming Growth Factor-beta 3 (TGF-β3) and a retention matrix into a mammal at a site where formation of bone is desired, wherein the bone formation is induced at a heterotopic site, and wherein the site is the rectus abdominis muscle of a primate.

* * * * *